US009320454B2

(12) United States Patent
Grodzki et al.

(10) Patent No.: US 9,320,454 B2
(45) Date of Patent: Apr. 26, 2016

(54) METHOD AND MAGNETIC RESONANCE APPARATUS TO GENERATE A SERIES OF MR IMAGES TO MONITOR A POSITION OF AN INTERVENTIONAL DEVICE

(71) Applicants: David Grodzki, Erlangen (DE); Bjoern Heismann, Erlangen (DE); Sebastian Schmidt, Weisendorf (DE)

(72) Inventors: David Grodzki, Erlangen (DE); Bjoern Heismann, Erlangen (DE); Sebastian Schmidt, Weisendorf (DE)

(73) Assignee: Siemens Aktiengesellschaft, Munich (DE)

( * ) Notice: Subject to any disclaimer, the term of this patent is extended or adjusted under 35 U.S.C. 154(b) by 648 days.

(21) Appl. No.: 13/630,155

(22) Filed: Sep. 28, 2012

(65) Prior Publication Data

US 2013/0076357 A1 Mar. 28, 2013

(30) Foreign Application Priority Data

Sep. 28, 2011 (DE) .......................... 10 2011 083 619

(51) Int. Cl.
| A61B 5/06 | (2006.01) |
| G01R 33/28 | (2006.01) |
| G01R 33/48 | (2006.01) |
| A61B 19/00 | (2006.01) |
| A61B 5/055 | (2006.01) |

(52) U.S. Cl.
CPC ............. *A61B 5/062* (2013.01); *A61B 19/5244* (2013.01); *G01R 33/286* (2013.01); *G01R 33/4816* (2013.01); A61B 5/055 (2013.01); A61B 2019/5236 (2013.01); A61B 2019/5265 (2013.01); G01R 33/4824 (2013.01)

(58) Field of Classification Search
None
See application file for complete search history.

(56) References Cited

U.S. PATENT DOCUMENTS

| 5,307,015 A * | 4/1994 | Kaufman et al. ............. 324/309 |
| 7,622,922 B2 | 11/2009 | Dannels |
| 2005/0073304 A1 * | 4/2005 | Feiweier et al. ............. 324/307 |
| 2006/0116574 A1 | 6/2006 | Wong et al. |
| 2008/0114235 A1 * | 5/2008 | Unal et al. ..................... 600/411 |
| 2008/0221428 A1 | 9/2008 | Flask et al. |
| 2011/0204892 A1 * | 8/2011 | Li et al. ......................... 324/309 |

FOREIGN PATENT DOCUMENTS

| DE | 42 19 610 C1 | 1/1994 |
| WO | WO 2010125486 A1 * | 11/2010 |

OTHER PUBLICATIONS

Heid et al., "Rapid Single Point (RASP) Imaging," Institute of Diagnostic Radiology, University of Bern, CH-3010 Bern, Swizerland, Siemens Medical Engineering, Henkestr. 127, D-91054 Erlangen, p. 684.

Nielles-Vallespin et al., 3D Radial Projection Technique With Ultrashort Echo Times for Sodium MRI: Clinical Applications in Human Brain and Skeletal Muscle, Magnetic Resonance in Medicine, vol. 57 (2007), pp. 74-81.

* cited by examiner

Primary Examiner — Tse Chen
Assistant Examiner — Lisa Kinnard
(74) Attorney, Agent, or Firm — Schiff Hardin LLP

(57) ABSTRACT

In a magnetic resonance (MR) method and system to generate a series of MR images to monitor the position of an interventional device located in an examination region, radial scanning of k-space is combined with other scans, in particular for the k-space center. The measurement time until the entirety of k-space corresponding to the imaging region is scanned is thereby markedly shortened in total. The short echo times that are possible with this reduce susceptibility artifacts in the reconstructed image data and enable a depiction of tissue or substances with very short T2 values, for example plastics. Due to the rapidly repeated excitation and acquisition of measurement data and the reconstruction of image data, it is possible to monitor a position of the intervention device in the examination region.

12 Claims, 4 Drawing Sheets

METHOD AND MAGNETIC RESONANCE APPARATUS TO GENERATE A SERIES OF MR IMAGES TO MONITOR A POSITION OF AN INTERVENTIONAL DEVICE

BACKGROUND OF THE INVENTION

1. Field of the Invention

The invention concerns a method to generate a series of MR images to monitor a position of an intervention apparatus located in an examination region, as well as a magnetic resonance apparatus and a non-transitory, computer-readable data storage medium encoded with programming instructions to implement such a method.

2. Description of the Prior Art

Magnetic resonance MR is a known modality with which images of the inside of an examination subject can be generated. Expressed simply, the examination subject is positioned within a strong, static, homogeneous basic magnetic field (also called a $B_0$ field) with field strengths of 0.2 Tesla to 7 Tesla and more, such that the nuclear spins of the examination subject orient along the basic magnetic field. To trigger magnetic resonances, radio-frequency excitation pulses (RF pulses) are radiated into the examination subject, the triggered magnetic resonance signals are measured, and MR images are reconstructed or spectroscopy data are determined based on these magnetic resonance signals. For spatial coding of the measurement data, rapidly switched magnetic gradient fields are superimposed on the basic magnetic field. The acquired measurement data are digitized and stored as complex numerical values in a k-space matrix. An associated MR image can be reconstructed from the k-space matrix populated with such values, for example by means of a multidimensional Fourier transformation.

For example, in medical interventions on examination subjects such as patients (such as biopsies or procedures to introduce a catheter or other artificial medical interventional devices) it is often desired to be able to monitor the course of these devices or instruments. Conventionally this is done using C-arm computed tomography systems. These use x-rays for imaging, which x-rays damage and stress both the exposed tissue and the person conducting the medical intervention. Furthermore, with C-arm computed tomography systems it is disadvantageous that the possible projection planes are limited to rotations only around a rotation axis (normally the longitudinal axis of a patient).

Therefore, there are efforts to also enable such monitoring by means of magnetic resonance. However, there are factors associated with magnetic resonance modalities that hinder a selection of the intervention devices (for example biopsy needles, catheters, etc.) that are used since these must be made of a material that is compatible with (for example) the basic magnetic field of the magnetic resonance system. Moreover, such interventional devices themselves often interfere with the excitation and/or acquisition of the measurement data, for example by inducing disruptions of the magnetic field and thus lead to artifacts (for example susceptibility artifacts) which make a precise localization of the interventional devices difficult or even impossible. This applies particularly to catheters, for example as are used in angiographies. These catheters normally are formed by plastic with guide wires made of metal, and therefore are barely visible or not visible at all in conventional MR exposures. Moreover, if monitoring takes place by means of magnetic resonance, the person conducting the interventional procedure is subjected to a high noise exposure since the typical MR examination sequences generate assessed sound pressure levels of well above 90 dB(A). Ear protectors are used to reduce the noise exposure, for example, but these are often perceived as disruptive.

In order to reduce artifacts in MR images, a significant effort is invested in the research and development of MR-compatible invention devices. In addition, it is sought to keep artifacts small by using sequences short echo times, or to process artifacts out of the data in the post-processing of the measurement data.

A number of MR-compatible markers for interventional devices are known. A selection of these is described in the United States Published Patent Application 2008/0221428 A1, for example. However, such specifically designed interventional devices are significantly more expensive and, due to the higher cost in the manufacturing, may possibly be more difficult to obtain than conventional interventional devices.

Sequences are known which enable a very short echo time. One example is the radial UTE ("Ultrashort Echo Time") sequence, for example as described in the article by Sonia Nielles-Vallespin "3D radial projection technique with ultrashort echo times for sodium MRI: Clinical applications in human brain and skeletal muscle", Magn. Res. Med. 2007; Vo. 57; pp. 74-81. In this type of sequence, after a wait period T_delay following a non-selective or slice-selective excitation, the gradients are ramped up and the data acquisition is begun simultaneously. The k-space trajectory that is scanned in such a manner after an excitation proceeds radially from the k-space center outwardly. Therefore, before the reconstruction of the image data from the raw data acquired in k-space can take place by means of Fourier transformation, the raw data must initially be converted into a Cartesian k-space grid, for example by regridding.

An additional approach in order to enable short echo times is to scan k-space in a point-like manner by detecting the free induction decay (FID) signal. Such a method is also designated as single point imaging since essentially only one raw data point in k-space is detected per RF excitation. One example of such a method for single point imaging is the RASP method ("Rapid Single Point (RASP) Imaging", P. Heid, M. Deimling, SMR, 3rd Annual Meeting, Page 684, 1995). According to the RASP method, at a fixed point in time after the RF excitation, a raw data point in k-space whose phase has been coded by gradients is read out at the "echo time" TE. The gradients modified by means of the magnetic resonance system for each raw data point or measurement point, and k-space is thus scanned point-by-point as is presented in FIGS. 1a and 1b herein.

SUMMARY OF THE INVENTION

An object of the present invention is to provide a method, a magnetic resonance system, and an electronically readable data medium that enable a fast generation and display of a series of MR images in which a position of an interventional device in an examination region can be determined.

A method according to the invention to generate a series of MR images to monitor a position of an intervention device located in an examination region includes the steps:

read out k-space corresponding to the examination region, includes the steps:

a) switching at least two phase coding gradients (Gx, Gy, Gz) in a respective spatial direction by means of a gradient system of the magnetic resonance system, b) after reaching the full strength of the switched phase coding gradients (Gx, Gy, Gz), radiating a non-slice-selective RF excitation pulse by means of a radio-frequency frequency antenna of the magnetic resonance system, c) after the time period t1 after the last radiated excitation pulse, acquiring echo signals by means of the radio-frequency antenna and store these as raw data points along the radial k-space trajectory predetermined by the strength of the phase coding gradients (Gx, Gy, Gz), d) repeating Steps a) through c) with different phase coding gradients (Gx, Gy, Gz) until k-space corresponding to the imaging area is read out in a first region (depending on the time t1) along radial k-space trajectories, and e) reading out k-space corresponding to the imaging area—which k-space is not covered by the first region of k-space, and which comprises at least the k-space center—in a different manner than described by Steps a) through d), and store these raw data points, reconstruct image data from the acquired raw data points of k-space by means of a system computer of the magnetic resonance system, wherein the reconstruction comprises a Fourier transformation, repeat the readout of k-space and the reconstruction of image data to generate multiple current MR images of the examination region, display the reconstructed image data at display means of the magnetic resonance system to determine a current position of the intervention device.

By switching the phase coding gradients and waiting until the switched phase coding gradients have reached their full strength before beginning the RF sending and the acquisition of echo signals (thus the acquisition of measurement data), the echo time—thus the time that extends between the excitation via an RF excitation pulse and the start of the acquisition of the measurement data—can be reduced in comparison to a UTE sequence in the entire k-space to be scanned radially. Echo signals of substances with very short T2 (such as plastics, for example) can therefore also be detected, and the repetition time (the time between two RF excitation pulses) can be reduced accordingly. MR images can therefore be created within a time period of less than a second, and even conventional intervention devices that are already commercially available (for example catheters and their guide wires) can be depicted.

Moreover, the measurement is less prone to disruptions—for example eddy currents induced in the gradient system during the change to its current feed—since measurement does not take place while the phase coding gradients are being ramped up. Measurement data can therefore be acquired with more precision.

Because only the region that includes the k-space center is read out in a different manner than the radial part in the first region, the measurement time for the entirety of k-space corresponding to the imaging region is markedly shortened overall, for example relative to pure single point imaging methods. The short echo times that are possible with this furthermore reduce susceptibility artifacts in the reconstructed image data since the influence of the magnetic field due to arising magnetizations takes up a certain amount of time. Furthermore, only symmetrical susceptibility artifacts are to be expected due to the radial acquisition (as well as the phase-coded acquisition in single point imaging), while in conventional phase-coded and frequency-coded measurements chemical shifts occur which asymmetrically distort a reconstructed MR image.

In one exemplary embodiment, the region which comprises the k-space center ($k_x=0$, $k_y=0$, $k_z=0$) that is important to the image reconstruction (contrast) is read out in a Cartesian manner, for example by means of a single point imaging method such as RASP. The precision of the scanning of the k-space center, and possibly of an area in k-space that surrounds the k-space center, can thereby be increased since the raw data read out there already lie on a Cartesian k-space grid, and such an error-plagued conversion as with the radially read-out raw data does not need to take place first before image data can be constructed from the raw data.

Overall, a particularly fast method with particularly short echo times—and therefore the depiction of tissue with small T2 values—are possible via the combination of radial and Cartesian read-out of k-space.

In an exemplary embodiment, the time period t1 that extends after the last radiated excitation pulse until the acquisition of the echo signals is equal to the minimum switch-over time $TE_{HW}$ between a transmission mode and a reception mode of the radio-frequency antenna. In the present method, the echo time t1 is thus limited at the lower end only by a hardware constant—the switch-over time $TE_{HW}$.

In another exemplary embodiment, the phase coding gradients are switched such that the image data reconstructed from the acquired raw data are projection images. The total acquisition time for such a set of raw data to reconstruct projection image data is short with the present method (on the order of a few 100 ms, for example approximately 250 ms), such that in particular a time-resolved presentation of the imaging area is possible. Multiple respective current MR images—for example four to 10 respective current MR images—can thus be generated within one second and be displayed successively. A real-time display of the examination region is thus possible.

In another exemplary embodiment, the phase coding gradients are switched automatically such that the projection direction of the projection image data is situated parallel or perpendicular to the intervention device located in the examination region, for example after the axis of the intervention device in the examination region has been determined by means of a preceding MR measurement or by means of other suitable means. A parallel alignment of the projection direction allows a good presentation of the target area (in the case of a biopsy, for example); an alignment of the projection direction perpendicular to the intervention device allows a good depiction of the intervention device itself, which can be desired given catheters, for example.

However, the phase coding gradients can also be switched such that the projection direction of the projection image data travels along an arbitrary predetermined axis. The predetermined axis can hereby be selected by a person operating the intervention device, for example, such that said intervention device in the examination region is visible at a desired relationship to said examination region.

The advantages and embodiments described with regard to the method analogously apply to the magnetic resonance system, and the electronically readable data medium.

DESCRIPTION OF THE PREFERRED EMBODIMENTS

Figure 1A:
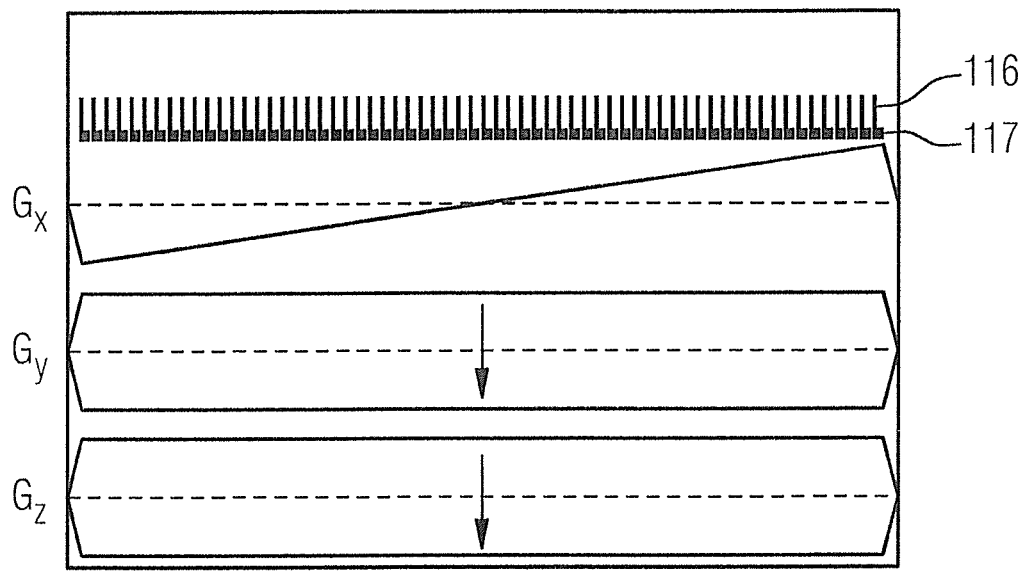
FIGS. 1a and 1b schematically illustrate the single point method RASP known according to the prior art.

A sequence to acquire a line in k-space is shown in FIG. 1a for the known single point RASP method. It is apparent that the two phase coding gradients $G_y$ and $G_z$ are activated with a constant strength while the strength of the third phase coding gradient $G_x$ increases continuously.

Figure 1B:
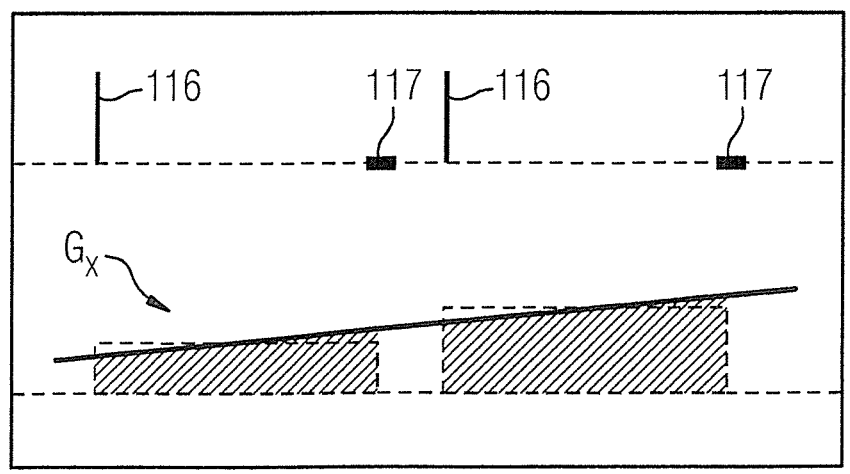

The acquisition of two raw data points in RASP is presented in detail in FIG. 1b. It is apparent that the echo time—i.e. the time interval from the RF excitation pulse 116 up to the beginning of the readout time period 117—is constant. Moreover, the phase coding gradient $G_x$ runs in stages from the bottom upward. The phase coding gradient $G_x$ to read out a raw data point is thereby kept constant, which means that the phase coding gradient $G_x$ is kept constant for the time period TE (echo time).

Figure 2:
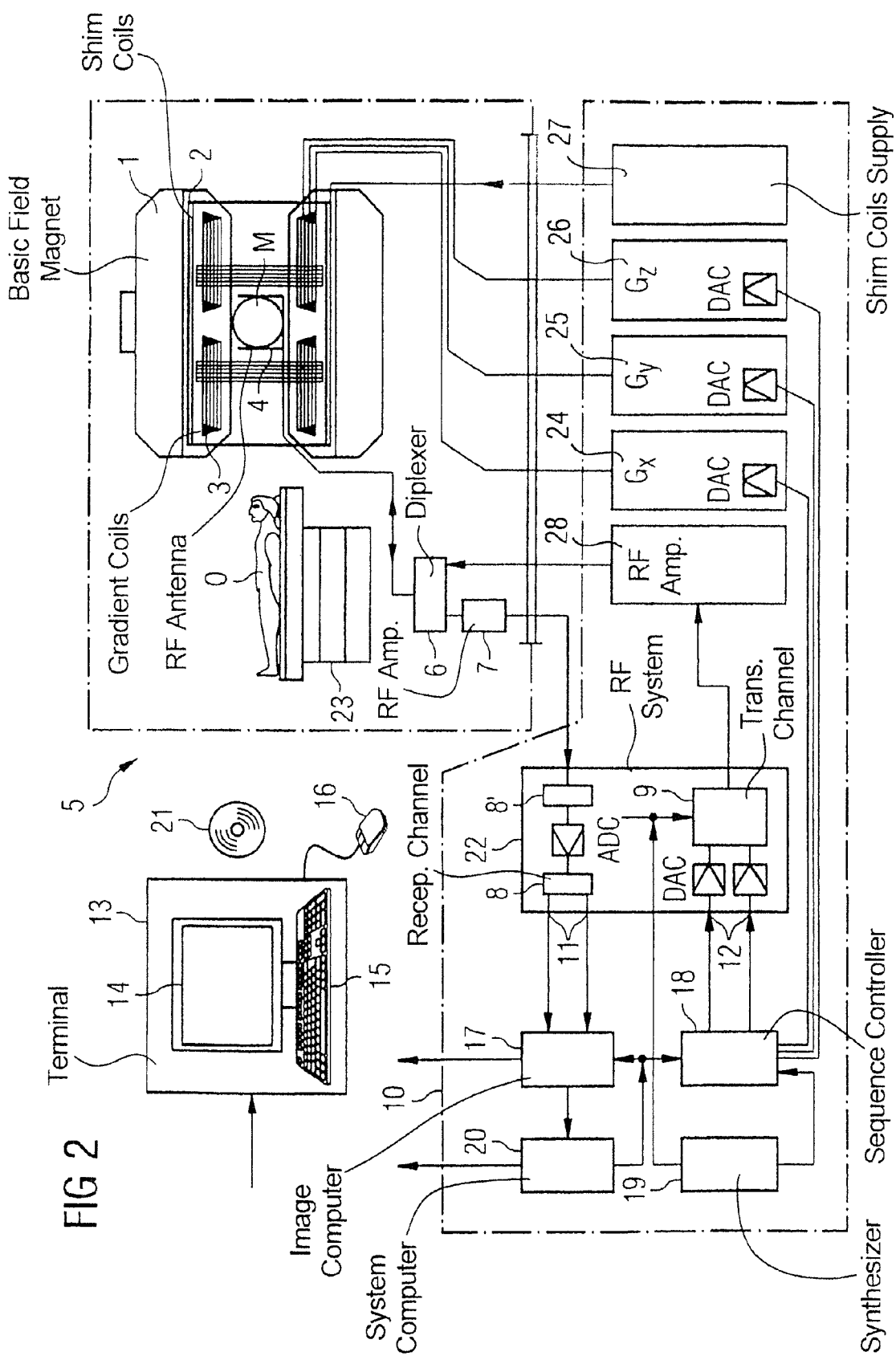
FIG. 2 schematically illustrates a magnetic resonance system according to an embodiment of the present invention.

FIG. 2 shows a schematic representation of a magnetic resonance system 5 (a magnetic resonance imaging or tomography apparatus). A basic field magnet 1 generates a temporally constant, strong magnetic field for polarization or alignment of the nuclear spins in an examination region of an examination subject U, for example a part of a human body that is to be examined that lies on a table 23 and is moved into the magnetic resonance system 5. The high homogeneity of the basic magnetic field that is required for the magnetic resonance measurement (data acquisition) is defined in a typically spherical measurement volume M into which the parts of the human body that are to be examined are introduced. To support the homogeneity requirements, and in particular to eliminate temporally variable influences, known as shim plates made of ferromagnetic material are mounted at a suitable point. Temporally variable influences are eliminated via shim coils 2 and a suitable controller 27 for the shim coils 2.

A cylindrical gradient coil system 3 that has three sub-windings is used in the basic magnetic field 1. Each sub-winding is supplied by a corresponding amplifier 24-26 with current to generate a linear gradient field in the respective direction of a Cartesian coordinate system. The first sub-winding of the gradient field system 3 generates a gradient $G_x$ in the x-direction; the second sub-winding generates a gradient $G_y$ in the y-direction; and the third sub-winding generates a gradient $G_z$ in the z-direction. The amplifiers 24-26 respectively comprise a digital/analog converter (DAC) which is controlled by a sequence controller 18 for time-accurate generation of gradient pulses.

Located within the gradient field system 3 is a radio-frequency antenna 4 that converts the radio-frequency pulses emitted by a radio-frequency power amplifier into an alternating magnetic field to excite the nuclei and align the nuclear spins of the subject to be examined or, respectively, of the region of the subject that is to be examined. The radio-frequency antenna 4 has one or more RF transmission coils and multiple RF reception coils in the form of an arrangement (annular, linear or matrix-like, for example) of coils. The alternating field emanating from the precessing nuclear spins—i.e. normally the nuclear spin echo signals caused by a pulse sequence made up of one or more radio-frequency pulses and one or more gradient pulses—is also transduced by the RF reception coils of the radio-frequency antenna 4 into a voltage (measurement signal), which is supplied via an amplifier 7 to a radio-frequency reception channel 8, 8' of a radio-frequency system 22. The radio-frequency system 22 furthermore has a transmission channel 9 in which the radio-frequency pulses are generated for the excitation of the nuclear magnetic resonance. The respective radio-frequency pulses are represented digitally in the sequence controller 18 as a series of complex numbers based on a pulse sequence predetermined by the system computer 20. This number series is supplied as real part and imaginary part via respective inputs 12 to a digital/analog converter (DAC) in the radio-frequency system 22, and from this to the transmission channel 9. In the transmission channel 9 the pulse sequences are modulated on a radio-frequency carrier signal whose base frequency corresponds to the resonance frequency of the nuclear spins in the measurement volume. The modulated pulse sequences are supplied to the RF transmission coil of the radio-frequency antenna 4 via an amplifier 28.

The switch-over from transmission operation to reception operation takes place via a transmission/reception diplexer 6. The RF transmission coil of the radio-frequency antenna 4 radiates the radio-frequency pulses into the measurement volume M to excite the nuclear spins and samples resulting echo signals via the RF reception coils. The correspondingly acquired magnetic resonance signals are phase-sensitively demodulated at an intermediate frequency in a first demodulator 8' of the reception channel of the radio-frequency system 22 and are digitized in the analog/digital converter (ADC). This signal is further demodulated to a frequency of zero. The demodulation to a frequency of zero and the separation into real part and imaginary part occur after the digitization in the digital domain in a second demodulator 8 which outputs the demodulated data via outputs 11 to an image computer 17. An MR image is reconstructed by the image computer 17 from the measurement data acquired in such a manner.

The administration of the measurement data, the image data and the control programs takes place via the system computer 20. Based on a specification with control programs, the sequence controller 18 controls the generation of the respective desired pulse sequences and the corresponding scanning of k-space. In particular, the sequence controller 18 controls the accurately-timed switching of the gradients, the emission of the radio-frequency pulses with defined phase amplitude and the reception of the magnetic resonance signals according to the method described herein.

The time base for the radio-frequency system 22 and the sequence controller 18 is provided by a synthesizer. The selection of corresponding control programs to generate a series of MR images (which are stored on a DVD 21, for example) as well as other inputs on the part of the user and the presentation of the generated MR images take place via a terminal 13 which comprises input means (for example a keyboard 15 and/or a mouse 16) to enable an input and display means (a monitor 14, for example) to enable a display, on which display means the generated series of MR images—in particular a current position of an intervention device I in the examination region U with time resolution—can be displayed. For example, via the input means a user can also enter a desired projection direction of generated projection image data and/or indicate an examination region to be examined (ROI; "region of interest"), and if necessary select those individual radio-frequency antennas of the radio-frequency antenna 4 which delivers an optimal signal-to-noise ratio (SNR) for the specified ROI. At least one additional display means (not shown) can also be comprised which can be arranged in proximity to the examination region U, such that in particular a person (not shown) conducting a medical intervention can see the MR images displayed at the additional display means during the medical intervention.

If the interventional device I located in the examination region is an interventional device I that includes an RF reception coil (for example as it is known from US2006/0116574), the echo signals can be acquired by means of this RF reception coil. An overlapping of echo signals from other structures that are not located in the acquisition area of the RF reception coil can be prevented. For example, given acquisition of projection data sets, structures that are located in the projection direction but not in the immediate environment of the intervention device I are not acquired with the RF reception coil of the intervention device I, whereby an overlapping of these structures with the structure of the intervention device I is prevented. This also applies to other local RF reception coils of the radio-frequency antenna 4. For example, given a projection data set along the longitudinal axis of a patient which was acquired by means of an RF reception coil arranged in the region of the abdomen of said patient, signals—for example from the head or other structures that are located in the projection direction but not in the immediate environment of the employed RF reception coil—are not aliased into the reconstructed MR image as well.

Figure 3:
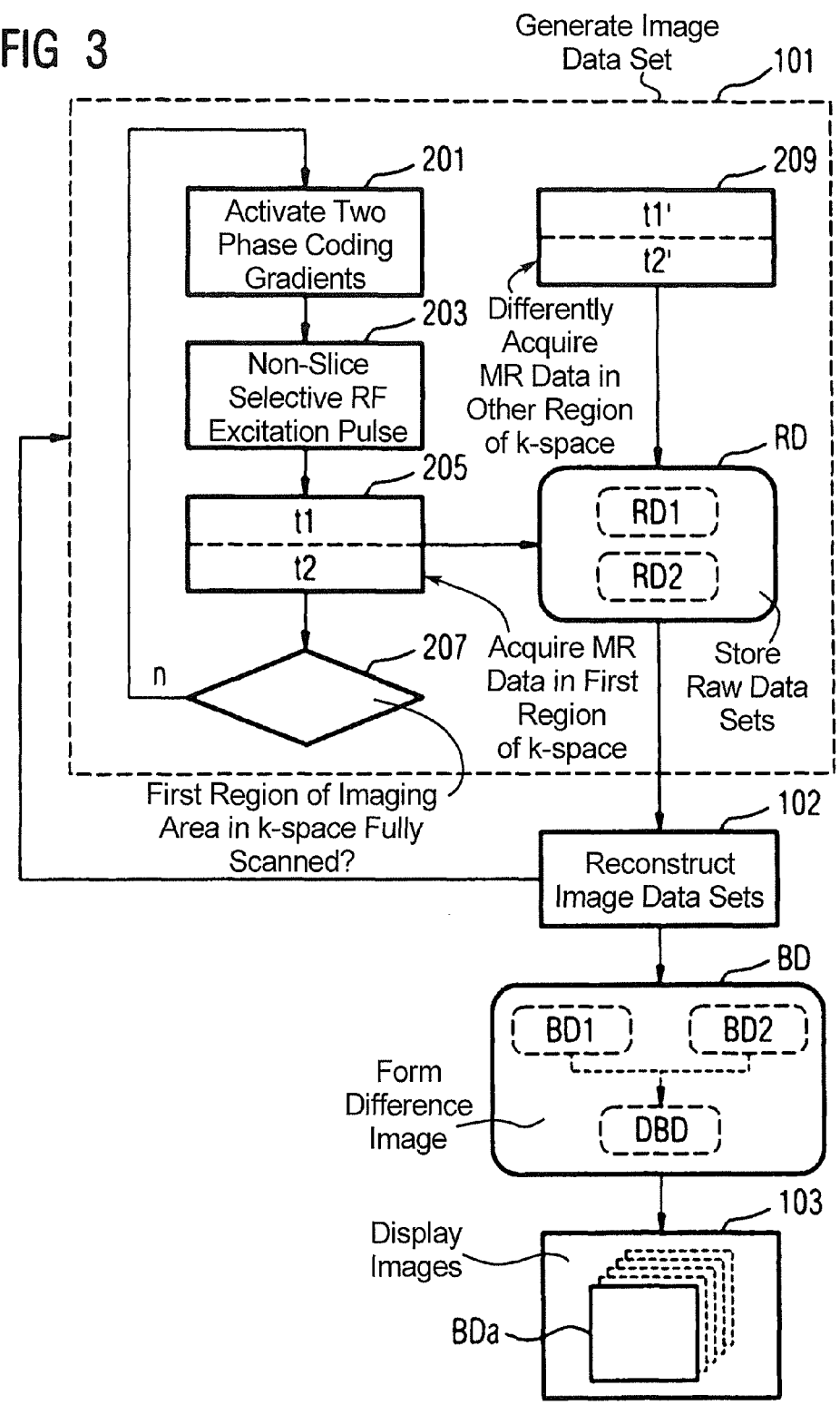
FIG. 3 is a flowchart of an embodiment of a method according to the invention to create a series of MR images of MR images to monitor a position of an intervention device located in an examination region.

An exemplary flowchart of a method according to the invention to create a series of MR images to monitor a position of an intervention device located in an examination region is schematically presented in FIG. 3.

Data entries are made in k-space corresponding to the imaging area in a first Step 101 to create an image data set.

For this purpose, at least two phase coding gradients ($G_x$, $G_y$, $G_z$) are switched in respective spatial direction by means of a gradient system of the magnetic resonance system (Block 201), and a non-slice-selective RF excitation pulse is radiated by means of a radio-frequency antenna of the magnetic resonance system (Block 202). If three phase coding gradients are switched, a three-dimensional image data set can be reconstructed in a conventional manner from the acquired raw data. If only two phase coding gradients are switched and (for example) a coding in the slice direction is omitted, a projection image data set can be reconstructed, wherein the projection direction can be arbitrarily selected in three-dimensional space.

After a time t1 after the last radiated excitation pulse, in which the phase coding gradients switched in Block 201 have already reached their full strength, echo signals are acquired by means of the radio-frequency antenna and stored as raw data points along the radial k-space trajectory predetermined by the strength of the phase coding gradients, for example as a raw data set RD in a system computer of the magnetic resonance system.

In one embodiment, echo signals are only acquired after the time t1 and stored as raw data in the raw data set RD. In a further embodiment, after the time t1 after each RF excitation pulse first echo signals are acquired and stored as raw data in a first raw data set RD1, and furthermore after a time t2 after the same RF excitation pulse at least one second echo signal is acquired and stored as an additional raw data point in a second raw data set RD2, wherein t2>t1. The second echo signal is generated in a known manner, for example via reversing the polarity of the gradients. The excitation and acquisition of a second echo signal can primarily be reasonable in the generation of three-dimensional image data sets, for example to improve the signal-to-noise ratio.

After all desired echo signals are acquired after an RF excitation pulse, and therefore after the corresponding k-space trajectory or trajectories has or have been read out, in Step 207 a check is made as to whether k-space corresponding to the imaging area has thus already been read out or not along radial k-space trajectories in a first region (depending on the time t1). If not ("n"), Block 201 is begun again, wherein phase coding gradients differing from the previously used phase coding gradients are switched.

K-space corresponding to the imaging area and that is not covered by the first region of k-space—which first region is scanned by means of Blocks 201 through 205—is read out at an arbitrary point in time, or at various points in time before, between or after the readout of the radial k-space trajectories, for example point by point by means of a single point imaging method (RASP, for example) or in another known manner (Block 209), and is likewise stored in the raw data set RD. If the raw data points that include the k-space center are thereby registered in a Cartesian manner, a regridding before the reconstruction of image data is superfluous.

In the readout of (entry of data into) k-space corresponding to the imaging area, the phase coding gradients can be varied continuously between the radiation of a first RF excitation pulse to acquire raw data points and a second RF excitation pulse to acquire additional raw data points of k-space corresponding to the imaging area. This means that the phase coding gradients are not ramped down after every acquisition of a radial k-space trajectory and ramped up again for the acquisition of the next k-space trajectory; rather, the phase coding gradients are only ramped up or, respectively, down further from the already assumed strength, until the strength required for the next acquisition is achieved. The eddy currents induced by the current flow of the gradient system that is required to generate the phase coding gradients can thus be reduced, which reduces the formation of noise which is caused by the forces that the eddy currents impinge upon the gradient system. The described sequence is therefore extremely quiet, such that a person conducting a medical intervention does not need to be protected against the noise development in the MR measurement, for example. This reduces the stress both in the person conducting the medical intervention and a patient to be examined.

It is advantageous to arrange the k-space trajectories to be read out such that the strength of the phase coding gradients must respectively only be varied as slightly as possible, so the noises caused by the change of the phase coding gradients can be further reduced in the measurement volume M of the magnetic resonance system.

Analogous to the exemplary embodiments dissolved above, for the raw data points that are not read out in a radial manner (for example by means of single point imaging methods) and that form the k-space center, after each RF excitation pulse a raw data point can be read out either only after a first echo time t1' and be stored in the first raw data set RD1, or after a first echo time t1' a first raw data point can be read out and stored in the first raw data set RD1. After a second echo time t2'—with t1'<t2'—a second raw data point is read out and stored in the second raw data set RD2. The generation of the second echo thereby takes place again in the known manner.

In a further Step 102, an image data set BD is reconstructed from the acquired raw data points which are stored in the raw data set RD, for example by means of the system computer of the magnetic resonance system using a Fourier transformation.

If the first and second raw data sets RD1 and RD2 have been acquired and stored, analogously a first image data set BD1 can be reconstructed from the first raw data set RD1 and an additional second image data set BD2 can be reconstructed from the second raw data set RD2, from which first image data set BD1 and second image data set BD2 a difference image can be calculated in a further exemplary embodiment. Due to the different echo times t1 and t2 with which the first and second raw data seta RD1 and RD2 have been acquired, it is possible to generate from the first and second image data sets BD1 and BD2 a difference image DBD in which exclusively tissues with a predetermined T2 are shown.

For example, such a difference image DBD can occur via per-pixel subtraction of the second image data set BD2 from the first image data set BD1 (or vice versa), possibly with a suitable weighting of at least one of the two image data sets BD1 and BD2, for example: DBD=a*BD1–b*BD2, with a and b weighting factors.

The weighting factors a and b are advantageously dependent on a time constant prevailing in the imaging area imaged with the image data sets BD1 and BD2, in particular depending on the T2 value prevailing in the imaging area. The difference image DBD can therefore be created such that optimally exclusively tissue with a defined (short) T2 are displayed.

As is illustrated by the arrow from 102 back to 101, the readout of k-space (Step 101) and the reconstruction of image data (Step 102) are repeated in order to create multiple current MR images of the examination region with the intervention device located therein. In this way at least one MR image is generated per second—advantageously multiple MR images per second.

The respective currently reconstructed image data BDa (abbreviated as the respective current MR image) is displayed at display means of the magnetic resonance system, as indicated by step 103, so that an observer can respectively assess a current position of the intervention device in the examination region.

Furthermore, the generated image data sets BD, BD1, BD2, DBD can, for example, be stored at a system computer of the magnetic resonance system for later use, post-processing or viewing, for example.

Figure 4:
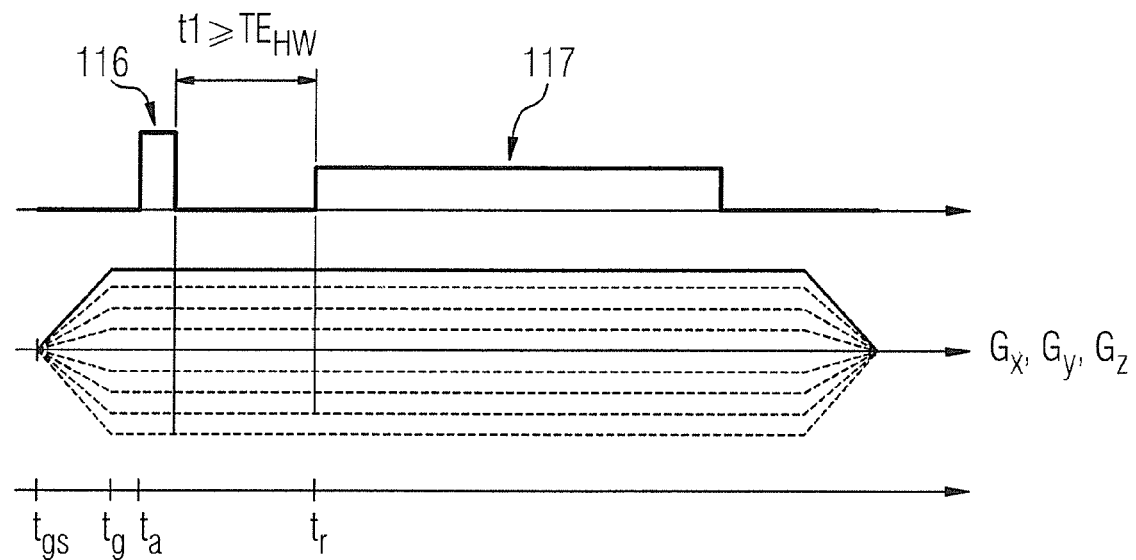
FIG. 4 schematically shows a portion of a sequence to acquire multiple raw data points on a radial k-space trajectory as it can be used in the method according to the invention.

The part of the sequence that serves to acquire multiple raw data points on a radial k-space trajectory as used in the method according to the invention is schematically presented in FIG. 4 (see FIG. 3, Blocks 201-205). At a point in time $t_{gs}$, at least two phase coding gradients $G_x$, $G_y$, $G_z$ are ramped up and reach their full strength at a point in time $t_g$. At a later point in time $t_a>t_g$, an RF excitation pulse 116 is radiated. After an echo time t1 after the RF excitation pulse 116 (that advantageously corresponds to the hardware-dependent minimum switching time between a transmission mode and a reception mode of a radio-frequency antenna $TE_{HW}$ that is used), the readout time period 117 to read out the echo signals is begun at the point in time $t_r$.

In the exemplary embodiment presented in FIG. 4, the phase coding gradients are switched before the RF excitation pulse is radiated.

The sequence described in FIGS. 3 and 4 to acquire the measurement data enables particularly short measurement times of even less than 500 microseconds (TE≤500 μs).

Figure 5:
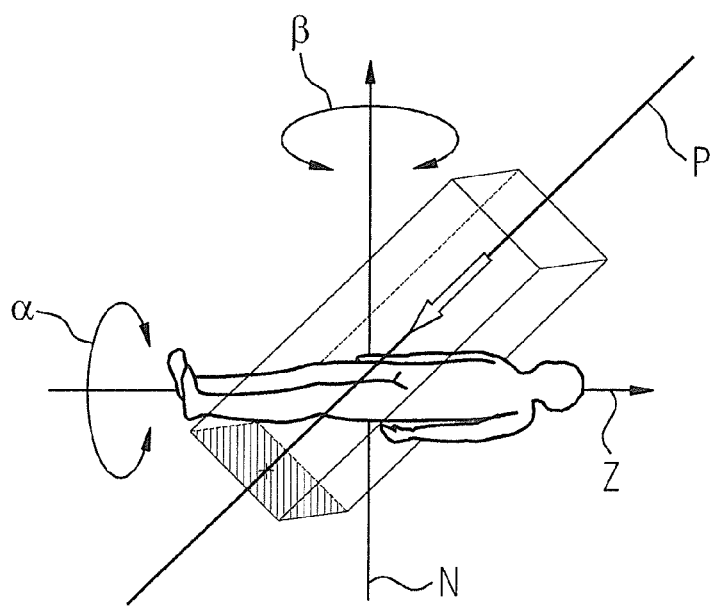
FIG. 5 schematically illustrates the projection directions that can be selected in connection with the method according to the invention given acquisition of a projection image data set.

If a projection image data set is acquired by means of the method described above, it is possible to select the projection direction freely in three-dimensional space. This is illustrated using FIG. 5.

In order to acquire MR images with a high time resolution, as already described above a coding in the slice direction can be omitted in the switched phase coding gradients, for example, and a projection image data set can be reconstructed. The MR image acquired in this way is a projection along the slice direction through the measured examination subject. For example, given MR measurements in three-dimensional space the projection direction P can be selected in that angles α and β are respectively selected around axes Z and N situated orthogonal to one another. The longitudinal axis of a patient to be examined can hereby be used as the axis Z, for example. In contrast to this, given C-arm computer tomographs only projections that correspond to a rotation around the shown axis Z are possible, meaning that only the angle α can be selected given C-arm computer tomographs.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method to generate a series of magnetic resonance (MR) images in order to monitor a position of an interventional device located in an examination region within an examination subject, comprising:
   operating an MR data acquisition unit to acquire MR data from an examination region of an examination subject in which an interventional device is located, by executing a first MR data acquisition procedure that comprises:
      (a) activating at least two phase-coding gradients in respective, different spatial directions with a gradient coil system of said MR data acquisition unit,
      (b) after the activated phase-coding gradients reach full strength, radiating a non-slice-selective radio-frequency (RF) excitation pulse with an RF transmission antenna of said MR data acquisition unit,
      (c) following a time t1 after the radiated RF excitation pulse, acquiring echo signals, resulting from nuclear spins excited by the radiated RF excitation pulse, with an RF reception antenna, and entering raw data points, representing said echo signals, into a memory representing k-space, along a radial k-space trajectory predetermined by the strength of the phase-coding gradients, k-space in said memory comprising an imaging area, corresponding to said examination region, and
      (d) repeating (a) through (c) with respectively different phase-coding gradients until a first region of k-space, dependent on t1, within said imaging area is filled with respective raw data points entered along respective radial k-space trajectories;
   operating said MR data acquisition unit to also acquire MR data from the examination region of the examination subject in which the interventional device is located, by executing a second MR data acquisition procedure that differs from said first MR data acquisition procedure, and making data entries of the MR data acquired in said second MR data acquisition procedure into a remainder of said imaging area in k-space, not covered by said first region, and comprising the center of k-space;
   in a computer, implementing a Fourier transformation of said raw data points in said first region and in said remainder of k-space to generate image data representing said examination region;
   repeating said operation of said MR data acquisition unit and said reconstruction of image data to generate multiple MR images of said examination region; and
   displaying said multiple MR images of said examination region at a monitor to allow visual determination therein of a current position of said interventional device.

2. A method as claimed in claim 1 comprising entering said raw data points in said remainder of k-space in said second MR data acquisition procedure according to a Cartesian arrangement.

3. A method as claimed in claim 1 comprising entering said raw data points into said remainder of k-space in said second MR data acquisition procedure according to a single point imaging method.

4. A method as claimed in claim 1 wherein said MR data acquisition unit exhibits a minimum switchover time between a transmission mode, in which said at least one RF excitation pulse is radiated, and a reception mode, in which said echo signals are detected, and setting said time t1 to be equal to said minimum switchover time.

5. A method as claimed in claim 1 wherein radiating said at least one RF excitation pulse comprises radiating at least a first RF excitation pulse that produces at least one echo signal during which raw data points in said imaging region are acquired, and a second RF excitation pulse that produces echoes during which additional raw data points of said imaging region are acquired.

6. A method as claimed in claim 1 comprising activating said phase-coding gradients to cause said image data reconstructed from the acquired raw data points to be projection image data.

7. A method as claimed in claim 6 comprising activating said phase coding gradients to cause a projection direction of said projection image data to be parallel to or perpendicular to said interventional device in said examination region.

8. A method as claimed in claim 6 comprising activating said phase-coding gradients to cause a projection direction of said projection image data to proceed along a predetermined axis.

9. A method as claimed in claim 1 comprising generating and displaying at least one of said multiple MR images per second.

10. A method as claimed in claim 1 wherein said interventional device comprises an RF reception coil, and employing said RF reception coil as said reception coil to detect said raw data points from said echo signals.

11. A magnetic resonance (MR) apparatus to generate a series of MR images in order to monitor a position of an interventional device located in an examination region within an examination subject, comprising:
   an MR data acquisition unit in which an examination subject is located, said subject comprising an examination subject in which an interventional device is located;
   a control computer configured to operate said MR data acquisition unit to execute a first MR data acquisition procedure that comprises:
      (a) activation of at least two phase-coding gradients in respective, different spatial directions with a gradient coil system of said MR data acquisition unit,
      (b) after the activated phase-coding gradients reach full strength, radiation of a non-slice-selective radio-frequency (RF) excitation pulse with an RF transmission antenna of said MR data acquisition unit,
      (c) following a time t1 after the radiated RF excitation pulse, acquisition of echo signals, resulting from nuclear spins excited by the radiated RF excitation pulse, with an RF reception antenna, and enter raw data points, representing said echo signals, into a memory representing k-space, along a radial k-space trajectory predetermined by the strength of the phase-coding gradients, k-space in said memory comprising an imaging area, corresponding to said examination region, and
      (d) repetition of (a) through (c) with respectively different phase-coding gradients until a first region of k-space, dependent on t1, within said imaging area is filled with respective raw data points entered along respective radial k-space trajectories;
   said control computer being configured to operate said MR data acquisition unit to also acquire MR data from the examination region of the examination subject in which the interventional device is located, by executing a second MR data acquisition procedure that differs from said first MR data acquisition procedure, and making data entries of the MR data acquired in said second MR data acquisition procedure into a remainder of said imaging area in k-space, not covered by said first region, and comprising the center of k-space;
   said control computer being configured to implement a Fourier transformation of said raw data points in said first region and in said remainder of k-space to generate image data representing said examination region;
   said control computer being configured to repeat said operation of said MR data acquisition unit and said reconstruction of image data to generate multiple MR images of said examination region; and
   a display monitor in communication with said control computer at which said control computer is configured to cause said multiple MR images of said examination region to be displayed in order to allow visual determination therein of a current position of said interventional device.

12. A non-transitory, computer-readable data storage medium encoded with programming instructions that, when said data storage medium is loaded into a computerized control and evaluation system of a magnetic resonance (MR) apparatus, which comprises an MR data acquisition unit, to cause said computerized control and evaluation system to:
   operate said MR data acquisition unit to acquire MR data from an examination region of an examination subject in which an interventional device is located, by executing a first MR data acquisition procedure that comprises:
      (a) activating at least two phase-coding gradients in respective, different spatial directions with a gradient coil system of said MR data acquisition unit,
      (b) after the activated phase-coding gradients reach full strength, radiating a non-slice-selective radio-frequency (RF) excitation pulse with an RF transmission antenna of said MR data acquisition unit,
      (c) following a time t1 after the radiated RF excitation pulse, acquiring echo signals, resulting from nuclear spins excited by the radiated RF excitation pulse, with an RF reception antenna, and entering raw data points, representing said echo signals, into a memory representing k-space, along a radial k-space trajectory predetermined by the strength of the phase-coding gradients, k-space in said memory comprising an imaging area, corresponding to said examination region,
      (d) repeating (a) through (c) with respectively different phase-coding gradients until a first region of k-space, dependent on t1, within said imaging area is filled with respective raw data points entered along respective radial k-space trajectories;
   operate said MR data acquisition unit to also acquire MR data from the examination region of the examination subject in which the interventional device is located, by executing a second MR data acquisition procedure that differs from said first MR data acquisition procedure, and making data entries of the MR data acquired in said second MR data acquisition procedure into a remainder of said imaging area in k-space, not covered by said first region, and comprising the center of k-space;

implement a Fourier transformation of said raw data points in said first region and in said remainder of k-space to generate image data representing said examination region;

repeat said operation of said MR data acquisition unit and said reconstruction of image data to generate multiple MR images of said examination region; and display said multiple MR images of said examination region at a monitor to allow visual determination of a current position of said interventional device.

* * * * *